US007989590B2

(12) United States Patent
Honma et al.

(10) Patent No.: US 7,989,590 B2
(45) Date of Patent: Aug. 2, 2011

(54) PEPTIDES THAT INCREASE COLLAGEN OR HYALURONIC ACID PRODUCTION

(75) Inventors: Yoichi Honma, Osaka (JP); Kazuaki Kikuchi, Osaka (JP); Hiroshi Uemura, Osaka (JP); Satoshi Inaoka, Osaka (JP); Shuichi Tsunetsugu, Osaka (JP)

(73) Assignee: Rohto Pharmaceutical Co., Ltd, Osaka (JP)

( * ) Notice: Subject to any disclaimer, the term of this patent is extended or adjusted under 35 U.S.C. 154(b) by 593 days.

(21) Appl. No.: 11/886,724

(22) PCT Filed: Mar. 17, 2006

(86) PCT No.: PCT/JP2006/305901
§ 371 (c)(1),
(2), (4) Date: Sep. 20, 2007

(87) PCT Pub. No.: WO2006/101187
PCT Pub. Date: Sep. 28, 2006

(65) Prior Publication Data
US 2009/0209728 A1     Aug. 20, 2009

(30) Foreign Application Priority Data

Mar. 22, 2005  (JP) ................................. 2005-081899
Oct. 24, 2005  (JP) ................................. 2005-308356

(51) Int. Cl.
*A61K 38/04*     (2006.01)
*C07K 5/00*      (2006.01)
*C07K 7/00*      (2006.01)
*C07K 16/00*     (2006.01)
*C07K 17/00*     (2006.01)

(52) U.S. Cl. ..................................................... 530/330

(58) Field of Classification Search ........................ None
See application file for complete search history.

(56) References Cited

U.S. PATENT DOCUMENTS

| 5,270,447 | A | * | 12/1993 | Liotta et al. | 530/326 |
| 5,516,891 | A | * | 5/1996 | Siwruk et al. | 530/330 |
| 6,610,836 | B1 | * | 8/2003 | Breton et al. | 536/23.1 |
| 2005/0025723 | A1 | | 2/2005 | Lipton | |
| 2006/0040870 | A1 | * | 2/2006 | LeBien et al. | 514/18 |

FOREIGN PATENT DOCUMENTS

| EP | 1 093 804 A | 4/2001 |
| EP | 1 093 804 A1 | 4/2001 |
| EP | 1 172 443 A1 | 1/2002 |
| JP | 7-194375 A | 8/1995 |
| JP | 9-176036 A | 7/1997 |
| JP | 10-182402 A | 7/1998 |
| JP | 2000-136147 A | 5/2000 |
| JP | 2001-206835 A | 7/2001 |
| JP | 2004-51533 A | 2/2004 |
| WO | WO-92/00091 | 1/1992 |
| WO | WO-98/09985 A | 3/1998 |
| WO | WO 98/10792 * | 3/1998 |
| WO | WO-00/56918 A1 | 9/2000 |
| WO | WO-02/068601 A | 9/2002 |
| WO | WO-03/017920 A | 3/2003 |
| WO | WO 03/106692 * | 6/2003 |
| WO | WO 2004/031733 A2 | 4/2004 |
| WO | WO-2005/090387 A | 9/2005 |

OTHER PUBLICATIONS

Kou Katayama et al. "Regulation of Extracellular Matrix Production by Chemically Synthesized Subfragments of Type I Collagen Carboxy Propeptide", Biochemistry 1991, 30, 7097-7104.
L. Lever et al. "Topical retinoic acid for treatment of solar damage", British Journal of Dermatology (1990) 122, 91-98.
Yasutomo Nishimori (Fundamental Technology Laboratories, POLA Chemical Industries"Photoaging and wrinkling: correlative changes of dermal collagen fiber bundles and wrinkles." pp. 36-42.
Markus Bohm et al. The Journal of Biological Chemistry vol. 279, No. 8, Issue of Feb. 20, pp. 6959-6966, 2004.
Shin-Seikagaku Jikken Koza 1 Tanpakushitsu VI (New Biochemistry Experimental Lecture 1 Protien VI), Chapter 1 (p. 3-29). Jun. 1992.
The Journal of biological Chemistry vol. 268, No. 14, Issue of May 15, pp. 9941-9944, 1993.
Jerry W. Slootstra et al. Structural aspects of antibody-antigen interaction revealed through small random peptide libraries. Molecular Diversity, 1 (1995) 87-96.
Ferenc Sebestyen et al., Binary Synthesis of Multicomponent Peptide Mixtures by the Portioning-mixing Technique. Journal of Peptide Science, vol. 1 26-30 (1995).
Journal of Biological Chemistry, vol. 273, No. 30, pp. 18848-18856, (1998).
Jerry W. Slootstra et al., Molecular Diversity, vol. 1, No. 2, 1995, pp. 87-96.
Sebestyen F. et al., Journal of Peptide Science, John Wiley and Sons Ltd. vol. 1, No. 1, 1995, pp. 26-30.
Kou Katayama, Journal of Biological Chemistry, American Society of Biochemical Biologists, vol. 268, No. 14, May 15, 1993, pp. 9941-9944.
Boehm M et al., Journal of Biolochemical Chemistry, American Society of Biolochemical Biologists, vol. 279, No. 8, Feb. 20, 2004, pp. 6959-6966.
Kagedal et al., "Sphingosine-Induced Apoptosis is Dependent on Lysosomal Proteases", Biochem. J., vol. 359, Pt. 2, pp. 335-343, 2001.

\* cited by examiner

*Primary Examiner* — Marcela M Cordero Garcia
(74) *Attorney, Agent, or Firm* — Birch Stewart Kolasch & Birch, LLP

(57) ABSTRACT

The present invention relates to a novel peptide having a specified amino acid sequence or its derivative, or a salt thereof. Further, the present invention relates to a composition containing the novel peptide or the like, a method of utilizing the novel peptide or the like, use of the novel peptide or the like, a polynucleotide encoding the novel peptide, or the like. The novel peptide of the present invention or its derivative, or a salt thereof can be utilized for enhancing production of at least one member selected from the group consisting of collagen and hyaluronic acid in a cell.

12 Claims, No Drawings

PEPTIDES THAT INCREASE COLLAGEN OR HYALURONIC ACID PRODUCTION

TECHNICAL FIELD

The present invention relates to a novel peptide having a specified amino acid sequence or its derivative, or a salt thereof. Further, the present invention relates to a composition containing the novel peptide or the like, a method of utilizing the novel peptide or the like, use of the novel peptide or the like, a polynucleotide encoding the novel peptide, or the like. The novel peptide of the present invention or its derivative, or a salt thereof can be utilized for enhancing production of at least one member selected from the group consisting of collagen and hyaluronic acid in a cell.

BACKGROUND ART

Conventionally, it has been known that a connective tissue of an animal contains, as a main component thereof, collagen, hyaluronic acid, elastin, chondroitin sulfate, heparan sulfate, dermatan sulfate, laminin or the like. Among them, collagen and hyaluronic acid play an important role in a connective tissue as described later.

In other words, collagen is a main protein constituting a connective tissue of an animal, and particularly, collagen occupies nearly 30% of a total protein of a human body. Since the main function of collagen lies in formation of a skeletal structure of a living tissue, collagen is widely distributed in skin, cartilage tissues, a cornea, the heart, the liver or the like as a main component constituting a skeletal structure of a tissue form of an animal. Since collagen specifically acts on adhesion of various kinds of cells, and differentiation or proliferation of a cell, and also has a role as a regulatory factor for cell function, decrease in collagen may cause various diseases, such as corneal disorders such as corneal ulcer, articular disorders such as rheumatism, arthritis, degenerative arthritis and osteoarthritis, and inflammatory diseases in some cases.

In a skin dermis extracellular matrix, formation of a network bundle from a collagen fiber maintains a tissue form. When a collagen fiber is matured and proliferated to proceed with cross-link formation, to give a thick and straight collagen fiber bundle, which in turn gives appropriate skin tautness in a young skin. However, in an aged skin, with the lowering of an activity (e.g. an activity for collagen production and the like) of fibroblast, since a collagen fiber in a dermis extracellular matrix is remarkably decreased and an abnormal aging cross-link is formed, skin becomes rigid, and original skin tautness rich in elasticity is undesirably lost. As a result, wrinkles and sagging are formed in the skin. Change in a collagen fiber bundle structure of a hairless mouse by photoaging has been studied in detail (see *Fragrance Journal*, 4, 36-37, 1998). The results show that in a hairless mouse irradiated with UVB, wrinkles are formed, a collagen fiber bundle structure is broken down, and skin elasticity is reduced, so as to match the formation of the wrinkles. In addition, it has also been known that collagen is excellent in the moisture retaining function.

In order to improve the state caused by decrease in collagen, various substances for enhancing collagen synthesis have been found. For example, retinoic acid (see, for example, R. Marks et al., British Journal of Dermatology, 122, 91-98, 1990), a preparation containing three kinds of amino acids consisting of glycine, proline and alanine (see, for example, Japanese Patent Laid-Open No. Hei 7-194375), a plant extract from licorice, mulberry bark, aloe, *Equisetam arvense*, *Lonicerae flos*, cork tree bark, leaf of *Artemisia princeps*, gentian or the like (see for example, Japanese Patent Laid-Open No. 2001-206835), TGF-b, ascorbic acids and the like have been known. In addition, as another substance for enhancing collagen synthesis, a peptide consisting of 182nd to 241st amino acid residues of type I procollagen (see, for example, K. Katayama et al., Biochemistry, 30, 7097-7104, 1991), and a Lys-Thr-Thr-Lys-Ser (SEQ ID NO: 21) peptide selected from the above-mentioned peptide consisting of 182nd to 241st amino acid residues of type I procollagen (see, for example, K. Katayama et al., J. Biol. Chem., 268(14), 9941-9944, 1990) have been known.

On the other hand, hyaluronic acid is a kind of acidic mucopolysaccharides, which is present in skin, cartilage, a joint fluid, an umbilical cord, an ocular vitreous body, or other connective tissues. Inter alia, in skin epidermis, there have been known that hyaluronic acid is widely distributed from a basal layer to a granular layer, and that hyaluronic acid supports a structure of an epidermis extracellular space, and is involved in transportation of a substance such as a nutrient or a waste from an epidermal basal layer to a horny cell layer, and serves as a trigger for enhancing turnover of an epidermal cell. In addition, it has also been known that hyaluronic acid has a strong water-retaining action that about 6 L of water can be retained in only 1 g of hyaluronic acid, and that by this action, hyaluronic acid plays a role in retaining moisture in an intercellular space. It has been known that hyaluronic acid is gradually decreased with aging, and this decrease also is one cause for aging of a skin such as forming wrinkles and sagging of skin, the lowering in elasticity of skin and skin tautness, skin dryness, or skin roughness as in the case of collagen. However, hyaluronic acid is a polymer compound, so that it is not easy to supply the hyaluronic acid to an epidermis from the outside of the skin and in order to supply hyaluronic acid to a portion such as between epidermal cells, it is important to enhance biosynthesis of hyaluronic acid within a living body.

In order to improve the state caused by a decrease in hyaluronic acid, various substances for enhancing hyaluronic acid synthesis have been found. For example, an aloe extract, an okra extract, a water-soluble β-1,3-glucan derivative, an yeast extract (Japanese Patent Laid-Open No. 2004-051533), an extract of a sea alga belonging to the genus *Callophyllis* in the family Kallymeniaceae, (Japanese Patent Laid-Open No. 2000-136147), a lavender extract (Japanese Patent Laid-Open No. Hei 10-182402), and an extract of a sea alga belonging to the genus *Durvillea* in the family Durvilleaceae (Japanese Patent Laid-Open No. Hei 09-176036) have been known.

BRIEF DESCRIPTION OF THE INVENTION

However, since the conventional material was not sufficiently satisfactory in safety and its effects, the development of a novel material which is safe and has an ability for significantly enhancing production of at least one member selected from the group consisting of collagen and hyaluronic acid, has been desired. In view of the conventional problems, an object of the present invention is to provide a novel material which is safe and has an ability for significantly enhancing production of at least one member selected from the group consisting of collagen and hyaluronic acid.

As a result of intensive studies in view of solving the problems mentioned above, the present inventors have found that a novel peptide having a specified amino acid sequence can be utilized as a novel material which is safe and has an ability for significantly enhancing production of at least one member selected from the group consisting of collagen and hyaluronic acid. The present invention has been perfected thereby.

Concretely, the gist of the present invention relates to:

[1] a peptide represented by the formula (I):

Leu-Glu-His    (I), or its derivative, or a salt thereof;

[2] a peptide, which has substitution and/or addition of one or more amino acids in the amino acid sequence as defined in the above [1], and which has an ability for enhancing production of at least one member selected from the group consisting of collagen and hyaluronic acid in a cell, or its derivative, or a salt thereof, with proviso that the peptide does not contain Lys-Thr-Thr-Lys-Ser (SEQ ID NO: 21);

[3] a peptide represented by the formula (II):

Leu-Glu-His-Ala (SEQ ID NO: 1)    (II), or its derivative, or a salt thereof;

[4] a peptide represented by the formula (III):

Leu-Glu-Lys-Ala (SEQ ID NO: 18)    (III), or its derivative, or a salt thereof;

[5] a peptide represented by the formula (IV):

Leu-Asp-His-Ala (SEQ ID NO: 19)    (IV), or its derivative, or a salt thereof;

[6] a peptide represented by the formula (V):

Leu-Glu-His-Ala-Phe (SEQ ID NO: 20)    (V), or its derivative, or a salt thereof;

[7] a composition containing the peptide or its derivative, or a salt thereof as defined in any one of the above [1] to [6];

[8] a method for enhancing production of at least one member selected from the group consisting of collagen and hyaluronic acid in a cell, by using the peptide or its derivative, or a salt thereof as defined in any one of the above [1] to [6] or the composition as defined in the above [7];

[9] use of the peptide or its derivative, or a salt thereof as defined in any one of the above [1] to [6] for the manufacture of a composition for enhancing production of at least one member selected from the group consisting of collagen and hyaluronic acid in a cell;

[10] a polynucleotide consisting of a nucleotide sequence encoding the peptide as defined in any one of the above [1] to [6];

[11] a polynucleotide consisting of an antisense sequence to a nucleotide sequence encoding the peptide as defined in any one of the above [1] to [6];

[12] a plasmid containing the polynucleotide as defined in the above [10] or [11];

[13] an expression vector containing the polynucleotide as defined in the above [10] or [11]; and

[14] a transformant containing the polynucleotide as defined in the above [10] or [11].

DETAILED DESCRIPTION OF THE INVENTION

According to the present invention, a novel material having an ability for enhancing production of at least one member selected from the group consisting of collagen and hyaluronic acid is provided. In addition, it is shown that the peptide of the present invention or its derivative, or a salt thereof does not significantly reduce the number of cells when brought into action on a cell. Therefore, according to the present invention, a novel peptide or its derivative, or a salt thereof is provided, which has an ability for enhancing production of at least one member selected from the group consisting of collagen and hyaluronic acid, and which can be used safely without showing cytotoxicity.

The present invention is a peptide represented by the formula (I):

Leu-Glu-His, or its derivative, or a salt thereof.

The present invention also provides a peptide characterized in that the peptide has substitution and/or addition of one or more amino acids in the amino acid sequence represented by the formula (I): Leu-Glu-His, and has an ability for enhancing production of at least one member selected from the group consisting of collagen and hyaluronic acid in a cell (wherein the peptide does not contain Lys-Thr-Thr-Lys-Ser (SEQ ID NO: 21)), or its derivative, or a salt thereof.

In the present specification, "a derivative of a peptide" refers to, for example, a derivative obtained by acetylation, palmitoylation, myristylation, amidation, acrylation, dansylation, biotinylation, phosphorylation, succinylation, anilide formation, benzyloxycarbonylation, formylation, nitration, sulfonation, aldehyde formation, cyclization, glycosylation, monomethylation, dimethylation, trimethylation, guanidylation, amidination, maleylation, trifluoroacetylation, carbamylation, trinitrophenylation, nitrotroponylation, or acetoacetylation of a peptide, and the like. Among them, palmitoylation is preferable, since it is expected to increase permeability into a cell, and acetylation of an N-terminus, amidation of a C-terminus and methylation of a C-terminus are also preferable, since they are expected to confer resistance against exopeptidase which degrades a peptide from a terminus, and thus increase stability in a living body.

In the present specification, a "salt" refers to any pharmacologically acceptable salt (including inorganic salt and organic salt) of a peptide or its derivative, and includes, for example, sodium salt, potassium salt, calcium salt, magnesium salt, ammonium salt, hydrochloride, sulfate, nitrate, organic salt (acetate, citrate, maleate, malate, oxalate, lactate, succinate, fumarate, propionate, formate, benzoate, picrate, benzenesulfonate and the like) and the like, preferably, ammonium salt, hydrochloride, sulfate and acetate, more preferably ammonium salt and acetate of a peptide or its derivative.

Substitution of an amino acid is preferably, but not limited specifically to, conservative amino-acid substitution, i.e., conservative substitution of an amino acid.

In the present specification, the term "conservative substitution of an amino acid" refers to a substitution between amino acids in each group shown in the following Table 1.

TABLE 1

| | |
|---|---|
| Acidic amino acids | Aspartic acid (D), Glutamic acid (E) |
| Basic amino acids | Arginine (R), Lysine (K), Histidine (H) |
| Hydrophilic amino acids | Serine (S), Threonine (T), Asparagine (N), Glutamine (Q) |
| Hydrophobic amino acids | Tryptophan (W), Phenylalanine (F), Valine (V), Leucine (L), Isoleucine (I), Methionine (M), Proline (P), Alanine (A) |
| Aromatic amino acids | Tyrosine (Y), Tryptophan (W), Phenylalanine (F) |
| Hydroxyamino acids | Serine (S), Threonine (T) |
| Sulfur-containing amino acids | Cysteine (C), Cystine, Methionine (M) |
| Small amino acids | Glycine (G), Alanine (A), Serine (S), Methionine (M), Threonine (T) |

Among them, preferred conservative substitution of an amino acid includes substitution between aspartic acid (D) and glutamic acid (E), substitution among arginine (R), lysine (K) and histidine (H), substitution between tryptophan (W) and phenylalanine (F), substitution between phenylalanine (F) and valine (V), substitution among leucine (L), isoleucine (I) and alanine (A), substitution between glycine (G) and alanine (A), and the like.

(Conservative) substitution of one or more amino acids refers to, preferably (conservative) substitution of one or several amino acids, more preferably (conservative) substitution of 1 to 3 amino acids, further preferably (conservative) substitution of 1 to 2 amino acids, even more preferably (conservative) substitution of one amino acid.

Addition of one or more amino acids refers to addition of preferably 1 to 22 amino acids, more preferably 1 to 12 amino acids, even more preferably 1 to amino acids, even more preferably 1 to 3 amino acids, still more preferably 1 to 2 amino acids.

The peptide having conservative substitution and/or addition of one or more amino acids in Leu-Glu-His (hereinafter referred to as LEH as shown in the 1-letter code of an amino acid, in some cases) includes, but not limited to, for example, those containing conservative substitution of one or more amino acids (for example, IEH, LDH, LDK, LEK and the like), and those having one or more amino acids added to LEH sequence (for example, LEHA (SEQ ID NO: 1), LEHW (SEQ ID NO: 22), LEHF (SEQ ID NO: 23), LEHV (SEQ ID NO: 24), LEHL (SEQ ID NO: 25), LEHI (SEQ ID NO: 26), LEHM (SEQ ID NO: 27), LEHG (SEQ ID NO: 28), LEHS (SEQ ID NO: 29), LEHT (SEQ ID NO: 30), ALEH (SEQ ID NO: 31), GLEH (SEQ ID NO: 32), SLEH (SEQ ID NO: 33), MLEH (SEQ ID NO: 34), TLEH (SEQ ID NO: 35), LEHAW (SEQ ID NO: 36), LEHAF (SEQ ID NO: 20), LEHAV (SEQ ID NO: 37), LEHAL (SEQ ID NO: 38), LEHAI (SEQ ID NO: 39), LEHAM (SEQ ID NO: 40), LEHAG (SEQ ID NO: 41), LEHAS (SEQ ID NO: 42), LEHAT (SEQ ID NO: 43), ALEHA (SEQ ID NO: 44), GLEHA (SEQ ID NO: 45), SLEHA (SEQ ID NO: 46), MLEHA (SEQ ID NO: 47), TLEHA (SEQ ID NO: 48), FLEHA (SEQ ID NO: 49), SLE-HHT (SEQ ID NO: 50), GLEHAL (SEQ ID NO: 51), DLE-HAL (SEQ ID NO: 52), QLEHAK (SEQ ID NO: 53), SLE-HAD (SEQ ID NO: 54), QLEHAR (SEQ ID NO: 55), EFLEHA (SEQ ID NO: 56), LEHAVV (SEQ ID NO: 57), DPELEHA (SEQ ID NO: 58), HLEHAAS (SEQ ID NO: 59), LEHASVD (SEQ ID NO: 60) and the like) and the like. Among them, preferred peptide includes IEH, LDH, LDK, LEK, LEHA (SEQ ID NO: 1), LEHF (SEQ ID NO: 23), LEHG (SEQ ID NO: 28), LEHAF (SEQ ID NO: 20), FLEHA (SEQ ID NO: 49), SLEHHT (SEQ ID NO: 50), GLEHAL (SEQ ID NO: 51), DLEHAL (SEQ ID NO: 52), QLEHAK (SEQ ID NO: 53), SLEHAD (SEQ ID NO: 54), QLEHAR (SEQ ID NO: 55), EFLEHA (SEQ ID NO: 56), LEHAVV (SEQ ID NO: 57), DPELEHA (SEQ ID NO: 58), HLEHAAS (SEQ ID NO: 59), LEHASVD (SEQ ID NO: 60) and the like, and more preferably, the peptides are LEHA (SEQ ID NO: 1) and LEHAF (SEQ ID NO: 20).

In addition, the peptide having conservative substitution and addition of one or more amino acids in LEH peptide, but not limited specifically to, includes as preferred examples, for example, IEHA (SEQ ID NO: 61), LDHA (SEQ ID NO: 19), LDKA (SEQ ID NO: 62), LEKA (SEQ ID NO: 18) and the like. As more preferred examples of such peptide includes a peptide having substitution and/or addition of one or more amino acids in LEHA (SEQ ID NO: 1) peptide, more preferably a peptide having conservative substitution and/or addition of one or more amino acids in LEHA (SEQ ID NO: 1) peptide. Here, (conservative) substitution and/or addition of one or more amino acids has the same meaning as described above.

Furthermore, a peptide having one or several amino acids deleted from a peptide having conservative substitution and/or addition of one or more amino acids in LEH peptide is also included in the peptide of the present invention, as far as the peptide has an ability for enhancing production of collagen or hyaluronic acid in a cell. Such peptide includes, for example, EHA, LHA, LEA and the like, which is a peptide having one amino acid deleted from LEHA (SEQ ID NO: 1) peptide.

In the present specification, the term "having an ability for enhancing production of at least one member selected from the group consisting of collagen and hyaluronic acid in a cell" means that when a peptide of interest or its derivative, or a salt thereof is brought into action on a cell, the amount of production of collagen, hyaluronic acid, or both in the cell is increased as compared with that in the case where the peptide of interest or its derivative, or a salt thereof is not brought into action on a cell. This term means that, for example, when the peptide of interest or its derivative, or a salt thereof is brought into action at a concentration of 10 µg/ml in a test for a culturing system of a human cell, the amount of production of collagen in a cell reaches, for example, about 110% or more, more preferably about 120% or more, even more preferably about 130% or more, as compared with that in the case where the peptide of interest or its derivative, or a salt thereof is not brought into action. This term also means that, for example, when the peptide of interest or the like is brought into action at a concentration of 100 µg/ml, the amount of production of hyaluronic acid in a cell reaches, for example, about 110% or more, more preferably about 120% or more, even more preferably about 130% or more, as compared with that in the case where the peptide of interest or the like is not brought into action. In a specific embodiment, the cell in regard to the above-mentioned term means a fibroblast or a keratinocyte, and, in a further specific embodiment, means a skin fibroblast or an epidermal keratinocyte.

The peptide of the present invention can be prepared in a method known in the art. For example, the peptide of the present invention may be synthesized by a chemosynthetic method (for example, solid phase method (for example, Fmoc method), liquid phase method or the like), or may be prepared by a method such as recombinant expression. The amino acid constituting the peptide of the present invention can be either L- or D-type, preferably L-type.

Furthermore, the peptide of the present invention can also be prepared by cutting out a peptide consisting of an amino acid sequence of interest from an amino acid sequence of a protein containing the amino acid sequence of interest by a known method such as protease treatment. For example, the protein containing LEH sequence and LEHA (SEQ ID NO: 1) sequence includes the proteins as shown in the following Table 2.

TABLE 2

| Source organism | Name of protein | Portion containing LEHA sequence | Sequence |
| --- | --- | --- | --- |
| Daucus carota | β-fructofuranosidase (EC3.2.1.26) isozyme I class 3 precursor, soluble | Residues 12-15 | LPSRDLEHASSYTP (SEQ ID NO: 6) |
| Lycopersicon esculentum | 3β-hydroxylase | Residues 134-137 | IFGSPLEHARQLWP (SEQ ID NO: 7) |

TABLE 2-continued

| Source organism | Name of protein | Portion containing LEHA sequence | Sequence |
| --- | --- | --- | --- |
| Solanum tuberosum | Chaperonin-60 beta subunit precursor | Residues 560-563 | VVRCCLEHAASVAK (SEQ ID NO: 8) |
| Oryza sativa | Putative chaperonin 60 beta | Residues 562-565 | VVRCCLEHAASVAK (SEQ ID NO: 9) |
| Glycine max | Glycinin G3 precursor | Residues 228-231 | FAPEFLEHAFVVDR (SEQ ID NO: 10) |
| Phaseolus vulgaris | Serine threonine kinase homolog COK-4 | Residues 334-337 | EVEVQLEHALSMQE (SEQ ID NO: 11) |
| Manihot esculenta | Flavonol 3-O-glucosyltransferase 7 (EC 2.4.1.91) (UDP-glucose flavonoid 3-O-glucosyltransferase 7) (Fragment) | Residues 168-171 | PQVEILEHAALGVF (SEQ ID NO: 12) |
| Prunus persica | MADS6 | Residues 93-96 | TGSWTLEHAKLKAR (SEQ ID NO: 13) |
| Fragaria x ananassa | UDP-glucose glucosyltransferase | Residues 304-307 | EIANALEHAGHRFL (SEQ ID NO: 14) |
| Strongylocentrotus purpuratus | Hyperpolarization-activated (Ih) channel | Residues 406-409 | VAINGLEHAHWWEQ (SEQ ID NO: 15) |
| Lethenteron japonicum | Homeoprotein LjEMX | Residues 193-196 | SQLLRLEHAFEKNH (SEQ ID NO: 16) |
| Mytilus galloprovincialis | Paramyosin | Residues 618-621 | DARSLLEHAERARK (SEQ ID NO: 17) |

A person skilled in the art can appropriately select a protease suitable for cutting out a peptide consisting of the amino acid sequence of interest from the amino acid sequence of the protein containing the amino acid sequence of interest, taking sequence specificity or the like of the protease into consideration. For example, in order to cut out LEH sequence and/or LEHA (SEQ ID NO: 1) sequence from the above-mentioned sequence derived from *Daucus carota* (SEQ ID NO: 6), a method for cutting out can be exemplified by concomitant use of thermolysin (derived from *Bacillus thermoproteolyticus*) and chymotrypsin (derived from bovine pancreas), or the like. In addition, for example, in order to cut out LEH sequence and/or LEHA (SEQ ID NO: 1) sequence from the above-mentioned sequence derived from *Solanum tuberosum* (SEQ ID NO: 8), the method can be exemplified by concomitant use of Protease M "Amano" G (derived from *Aspergillus oryzae*: manufactured by Amano Enzyme, Inc.) and the above-mentioned thermolysin, or the like. In addition, for example, in order to cut out LEH sequence and/or LEHA (SEQ ID NO: 1) sequence from the above-mentioned sequence derived from *Oryza sativa* (SEQ ID NO: 9), the method can be exemplified by concomitant use of the above-mentioned Protease M "Amano" G and the above-mentioned thermolysin, or the like. In addition, for example, in order to cut out LEH sequence and/or LEHA (SEQ ID NO: 1) sequence from the above-mentioned sequence derived from Glycine max (SEQ ID NO: 10), the method can be exemplified by use of the above-mentioned thermolysin, or the like. In addition, for example, in order to cut out LEH sequence and/or LEHA (SEQ ID NO: 1) sequence from the above-mentioned sequence derived from Phaseolus vulgaris (SEQ ID NO: 11), the method can be exemplified by concomitant use of the above-mentioned chymotrypsin and the above-mentioned thermolysin, or the like. In addition, for example, in order to cut out LEH sequence and/or LEHA (SEQ ID NO: 1) sequence from the above-mentioned sequence derived from *Manihot esculenta* (SEQ ID NO: 12), the method can be exemplified by concomitant use of the above-mentioned chymotrypsin and the above-mentioned thermolysin, or the like. In addition, for example, in order to cut out LEH sequence and/or LEHA (SEQ ID NO: 1) sequence from the above-mentioned sequence derived from *Lethenteron japonicum* (SEQ ID NO: 16), the method can be exemplified by concomitant use of trypsin (derived from swine pancreas) and the above-mentioned thermolysin, or the like. The combination of a protein containing the amino acid sequence of interest and a protease is not limited to the above-mentioned combinations, and preferred combination includes a combination of soy protein (protein derived from Glycine max) and thermolysin.

The reaction conditions used when hydrolyzing a protein with a protease are not limited specifically, and can be appropriately selected by a person skilled in the art according to the common general technical knowledge. For example, when using a commercially available protease, the reaction conditions can be selected according to the instruction thereof. Generally, a reaction temperature of 30° to 80° C., preferably 40° to 70° C., more preferably 50° to 60° C. can be used. In addition, generally, a reaction time of 2 to 30 hours, preferably 3 to 24 hours, more preferably 10 to 20 hours, especially preferably 12 to 18 hours can be used. A reaction pH is preferably around an optimal pH of the protease used. Means for terminating the reaction is also not limited specifically, and a known method can be employed. Such means include, for example, heat treatment such as heating at 85° C. for 15 minutes or heating at 100° C. for 5 minutes, and the like.

After hydrolysis treatment with a protease, the peptide of interest can be obtained by purifying in accordance with means known in the art. As such known means, for example, strong acid ion exchange resin, octadecylsilica (ODS) resin or the like can be utilized. For example, the peptide of interest can be purified by adsorbing an aqueous solution of the peptide treated with a protease to ODS resin and eluting the peptide with an organic solvent (for example, acetonitrile or the like) at any concentration. Alternatively, for example, the peptide of interest can be purified by adsorbing an aqueous solution of the peptide treated with a protease to strong acid ion exchange resin and eluting the peptide with an eluate (for example, a solution of sodium chloride, potassium chloride or the like) having a salt concentration of 0.18 M to 0.25 M, more preferably 0.20 M to 0.23 M.

Thus, a peptide obtained by hydrolyzing a native protein with a protease is advantageous from the viewpoint of cost, as compared with that in the case of manufacturing by chemosynthetic method. Furthermore, the peptide obtained by hydrolyzing a native protein with a protease is assumed to be safer for a living body. Therefore, the peptide thus obtained can be suitably used for a medicine for internal application, a food, cosmetics for sensitive skin, a feed and the like of which application to a living body requires higher safety.

The derivative of the peptide of the present invention can be prepared by a method known in the art. For example, the method is exemplified as follows, taking acetylation of an N-terminus of LEH peptide, for instance (according to solid-phase synthesis method by Fmoc method (L. A. Carpino, G. Y. Han, *J. Am. Chem. Soc.,* 92, 5748 (1970)). First, the C-terminus of Fmoc-His(1-Trt)-OH is bound to resin for solid-phase synthesis, and thereafter a protecting group (Fmoc) is removed by piperidine treatment. Subsequently the obtained resin is neutralized and washed, and Fmoc-Glu(OtBu)-OH is introduced into the N-terminus of His. Next, the protecting group (Fmoc) is removed by piperidine treatment, and the obtained resin is neutralized and washed again. Thereafter, N-acetyl-leucine is introduced into the N-terminus of Glu. A peptide chain is cut out from the obtained resin, and deprotection is carried out by cleaving Trt group of His and tBu group of Glu with TFA (trifluoroacetic acid). Finally, purification is carried out by removing an unreacted substance by preparative HPLC, to give LEH of which N-terminus is acetylated. It is clear for a person skilled in the art that any derivative can be prepared by appropriately modifying the above-mentioned method, and that, for example, when N terminus-palmitoylated LEH is prepared, the above-mentioned N-acetyl-leucine may be changed to N-palmitoyl-leucine.

The salt of the peptide of the present invention can also be easily prepared by a person skilled in the art by any method known in the art.

The peptide of the present invention or its derivative, or the salt thereof thus obtained can be used for enhancing production of at least one member selected from the group consisting of collagen and hyaluronic acid in a cell.

As shown in the following Examples, it is confirmed that culturing skin fibroblast in a culture solution to which such peptide or its derivative or a salt thereof is added results in increase in the amount of production of type I collagen in the cell, and that culturing an epidermal keratinocyte in the culture solution results in increase in the amount of production of hyaluronic acid in the cell.

The present invention also provides a composition characterized in that the composition contains the above-mentioned peptide or its derivative, or a salt thereof. Due to such characteristics, the composition can be used suitably, for example, as a pharmaceutical composition, a food, cosmetics or a feed, and furthermore, as a research reagent for elucidating physiological conditions associated with collagen or hyaluronic acid.

The pharmaceutical composition includes, for example, a therapeutic agent or a prophylactic agent for a disease caused by decrease in the amount of collagen and/or hyaluronic acid in a mammal represented by human. Specifically, the composition of the present invention can be suitably used as a therapeutic agent and/or prophylactic agent for an articular disease such as rheumatoid arthritis, degenerative arthritis or osteoarthritis, or as a prophylactic agent and/or therapeutic agent for wrinkle or sagging of skin due to exposure to ultraviolet light, aging or the like, and furthermore, as a prophylactic agent and/or therapeutic agent for decrease in elasticity or tautness of skin.

The food includes, for example, a food for ameliorating or preventing conditions caused by decrease in the amount of collagen and/or hyaluronic acid in a mammal represented by human. Specifically, the composition of the present invention can be suitably used as a food for amelioration or prevention of symptoms such as arthralgia, or as a food for amelioration or prevention of wrinkle or sagging of skin due to exposure to ultraviolet light, aging or the like, and furthermore, as a food for amelioration or prevention of decrease in elasticity or tautness of skin.

The cosmetics include, for example, cosmetics for prevention and/or amelioration of wrinkle or sagging of skin due to exposure to ultraviolet light, aging or the like, and cosmetics for prevention and/or amelioration of decrease in elasticity or tautness of skin.

The feed includes, for example, a feed for ameliorating or preventing conditions caused by decrease in the amount of collagen and/or hyaluronic acid in livestock such as bovid, swine, poultry, sheep, and horse or pet animals such as dogs and cats. Specifically, the composition of the present invention can also suitably used as a feed for ameliorating or preventing various diseases caused by decrease in the amount of collagen and/or hyaluronic acid such as corneal disorders such as corneal ulcer, articular disorders such as rheumatism, arthritis, degenerative arthritis and osteoarthritis, and inflammatory disease.

The content of the above-mentioned peptide or its derivative, or a salt thereof in the composition of the present invention varies dependent on the kind of the peptide or the like, dosage form and the like of the composition. Generally, from the viewpoint of obtaining great effect of enhancing production of collagen and/or hyaluronic acid, the content is preferably 0.0001 to 70% by weight, more preferably 0.001 to 50% by weight, even more preferably 0.001 to 20% by weight, still more preferably 0.01 to 10% by weight, still more preferably 0.05 to 10% by weight, still more preferably 0.12 to 10% by weight.

The composition of the present invention can be prepared by appropriately combining a carrier, a base and/or an additive or the like usually used in the field of formulation, food or the like in addition to the above-mentioned peptide or its derivative, or a salt thereof, within the range where an object of the present invention can be achieved.

In one embodiment, the present composition can be prepared by combining those obtained by once purifying the above-mentioned peptide or its derivative, or a salt thereof so as to have a concentration of, for example, 0.05% by weight or more, preferably 0.08% by weight or more, more preferably 0.1% by weight or more, even more preferably 0.12% by weight or more, so as to have the above-mentioned content.

The carrier can be used in combination of one or more kinds of, for example, sugars (for example, mannitol, lactose, dextran or the like), celluloses (for example, hydroxypropyl cellulose, methyl cellulose, crystalline cellulose or the like), poorly water-soluble gums (for example, gum arabic, tragacanth gum or the like), cross-linked vinyl polymers, lipids or the like.

The base can be used in combination of one or more kinds of, for example, water, fats and oils, mineral oils, waxes, fatty acids, silicone oils, sterols, esters, metallic soaps, alcohols or the like.

The additive can be used in combination of one or more kinds of, for example, surfactants, solubilizing component, emulsifier, oily component, stabilizer, thickener, preservative, binder, lubricant, dispersing agent, pH regulator, moisturizer, ultraviolet absorbent, chelating agent, percutaneous-absorption enhancer, antioxidant, disintegrating agent, plasticizer, buffer, vitamins, amino acids, coloring agent, perfuming agent or the like.

Furthermore, in order to add other useful action if needed, the composition of the present invention may contain a combination of one or more kinds of various components such as skin-lightening component, anti-inflammatory component, antibiotic component, cell-activating component, astringent component, antioxidant component, acne-ameliorating component, component for enhancing synthesis of a biological component such as collagen, component for enhancing circulation, moisturizing component and antiaging component.

The composition of the present invention can take any dosage form such as an agent for external application (including cosmetics), an agent for internal application (including a food and feed) and the like, and can be used preferably as an agent for external application.

The agent for external application can be used in any form such as, for example, liquid, emulsion, cream, lotion, paste, mousse, gel, sheet (supported by a substrate), aerosol and spray.

The cosmetics can be used in any form such as, for example, cosmetics for basic skin care such as lotion, emulsion, cream, oil and mask, as well as makeup such as foundation, blusher and lipstick, and furthermore, cleansing preparation such as face wash, cleansing preparation and body-cleansing preparation, and bath agent.

The agent for internal application (including a food and a feed) can be used in any form such as, for example, tablet, pill, granule, fine granule, powder, hard capsule, soft capsule, dry syrup, solution (including drinkable preparation, suspension and syrup), gel preparation, liposome preparation, extract preparation, tincture, lemonade preparation and jelly preparation.

In addition, in the case of a food, the composition can be provided in any general form of a food such as bread, noodles, ready-prepared foods, processed meat products (for example, ham, sausage or the like), processed marine products, seasonings (for example, dressing or the like), dairy products, confectioneries (for example, biscuit, candy, jelly, ice cream or the like), soup and juice. When producing into such form, the peptide of the present invention or its derivative, or a salt thereof can be appropriately combined by a method known by a person skilled in the art, depending on the properties and the like of the food of interest.

The feed is not limited specifically, since the feed can be used in any form.

The composition of the present invention can be used for enhancing production of at least one member selected from the group consisting of collagen and hyaluronic acid in a cell, utilizing the ability of the above-mentioned peptide or its derivative, or the salt thereof, for enhancing production of collagen and/or hyaluronic acid in a cell.

The present invention further provides a method for enhancing production of at least one member selected from the group consisting of collagen and hyaluronic acid in a cell, characterized in that the above-mentioned peptide or its derivative, or the salt thereof, or the above-mentioned composition is used.

In the method of the present invention, the above-mentioned peptide or its derivative, or the salt thereof, or the above-mentioned composition may be used in an effective amount or more for obtaining the enhancing effect for production of at least one member selected from the group consisting of collagen and hyaluronic acid.

Specifically, the amount of the above-mentioned peptide or its derivative, or the salt thereof used in the method of the present invention is usually, in the case of an agent for external application, preferably about 0.1 µg to 2 g/day per adult weighing about 50 kg. The amount used in the case of an agent for internal application is usually, preferably about 0.001 mg to 10,000 mg/day, more preferably about 1 to 1,000 mg/day, even more preferably about 1 to 100 mg/day, per adult weighing about 50 kg.

The method of the present invention may further comprise the step of applying the above-mentioned peptide or its derivative, or the salt thereof, or the above-mentioned composition to skin. The amount of the above-mentioned peptide or its derivative, or the salt thereof applied to skin in this case is preferably about 1 ng to 500 µg/cm$^2$, more preferably about 0.01 to 50 µg/cm$^2$, even more preferably about 0.1 to 10 µg/cm$^2$.

The present invention further provides use of the above-mentioned peptide or its derivative, or the salt thereof for manufacture of a composition for enhancing production of at least one member selected from the group consisting of collagen and hyaluronic acid in a cell, preferably a composition which can be used as an agent for external application.

The above-mentioned peptide or its derivative, or the salt thereof may be used so as to have the above-mentioned content in the composition.

The present invention further provides a polynucleotide characterized in that the polynucleotide consists of a nucleotide sequence encoding the above-mentioned peptide.

The polynucleotide of the present invention is not limited specifically, as long as the polynucleotide encodes the above-mentioned peptide. For example, as a polynucleotide encoding LEHA (SEQ ID NO: 1), any sequence which is obvious to encode LEHA (SEQ ID NO: 1) according to the genetic code table can be appropriately used depending on codon usage and the like. Preferably, the polynucleotide is exemplified by the following sequence:

```
TTG GAA CAT GCG        (SEQ ID NO: 2)

TTG GAA CAT GCA        (SEQ ID NO: 3)

CTT GAA CAC GCG        (SEQ ID NO: 4)

CTG GAG CAC GCA        (SEQ ID NO: 5)
```

The polynucleotide of the present invention can be prepared by a method known in the art. For example, the polynucleotide can be prepared using a commercially available DNA synthesizer (for example, Applied Biosystems 3400 DNA synthesizer, manufactured by Applied Biosystems).

Using a polynucleotide obtained as described above, a plasmid or an expression vector described below can be prepared.

The present invention further provides a polynucleotide characterized in that the polynucleotide consists of an antisense sequence to a nucleotide sequence encoding the above-mentioned peptide.

Such polynucleotide can also be prepared in the same manner as described above.

The polynucleotide of the present invention can be utilized for expressing the above-mentioned peptide by gene engineering, or in gene therapy or the like, or as a reagent for elucidating physiological conditions associated with collagen or hyaluronic acid.

Furthermore, using such polynucleotide, a plasmid or an expression vector of the present invention described below can be prepared.

The present invention further provides a plasmid characterized in that the plasmid contains the above-mentioned polynucleotide.

The plasmid of the present invention can be prepared by incorporating the polynucleotide of the present invention to a known plasmid, including, but not limited specifically to, for example, pBR plasmid, pUC plasmid or the like, using a general technique for molecular biological experiment.

The present invention further provides an expression vector characterized in that the expression vector contains the polynucleotide of the present invention.

The expression vector of the present invention can be prepared by incorporating the polynucleotide of the present invention to a known vector, including, but not limited specifically to, for example, pcDNA3, pSD64, λ phage vector or the like using a general technique for molecular biological experiment so that the polynucleotide can be expressed.

Using the plasmid or an expression vector obtained as described above, a transformant described below can be prepared.

The present invention further provides a transformant characterized in that the transformant contains the above-mentioned polynucleotide.

The transformant of the present invention can be obtained by introducing the above-mentioned plasmid or expression vector into a desired host, incorporating the above-mentioned polynucleotide directly into a chromosome of a host, or the like. The host is not limited particularly, and, for example, *E. coli*, yeast, insect cell, animal cell or the like can be used as the host. As a method for introducing the expression vector into the host, a known method such as, for example, calcium treatment method, protoplast method, electroporation method, or DEAE dextran method may be used.

The above-mentioned peptide can also be obtained by culturing the transformant obtained as described above under appropriate conditions to express the above-mentioned peptide and purifying the peptide.

EXAMPLES

The present invention will be described hereinbelow on the basis of Examples, Comparative Examples and Reference Examples, but the present invention is not limited to these Examples and the like at all.

Example 1

Preparation of LEH

1) Synthesis of Peptide

A peptide was synthesized by solid-phase synthesis method by Fmoc method using an automatic peptide synthesizer (manufactured by SHIMADZU CORPORATION: PSSM8). Specific procedures are as follows: First, the C-terminus of Fmoc-His(1-Trt)-OH was bound to a resin for solid-phase synthesis, and thereafter the protecting group (Fmoc) was removed by piperidine treatment. Subsequently, this resin was neutralized and washed, and Fmoc-Glu(OtBu)-OH was introduced into the N-terminus of His. Next, the protecting group (Fmoc) was removed by piperidine treatment, and this resin was neutralized and washed again. Thereafter, Fmoc-Leu-OH was introduced into the N-terminus of Glu. Next, the protecting group (Fmoc) was removed by piperidine treatment, and a peptide chain was cut out from this resin. Deprotection was carried out by cleaving Trt group of His and tBu group of Glu with TFA (trifluoroacetic acid). Finally, purification was carried out by removing an unreacted substance by preparative HPLC, to give LEH.

2) Purity Assay for Synthetic Peptide

The resulting purified product was subjected to reversed phase high-performance liquid chromatography for analysis [column: μBondasphere 5μ C18-100 Å (inner diameter: 3.9 mm, length: 150 mm), manufactured by Waters Corporation; mobile phase: gradient of solvent A containing 0.1% trifluoroacetic acid and solvent B containing 0.1% trifluoroacetic acid and 90% acetonitrile from minute 0 (solvent B=7%) to minute 20 (solvent B=12%); flow rate: 1 ml/min.; detection method: absorbance at wave length of 220 nm]. A single sharp peak appeared at minute 13.1, and the purity was 99%.

Example 2

Preparation of LEHA (SEQ ID NO: 1)

Peptide LEHA (SEQ ID NO: 1) was synthesized and purified in the same manner as the method described in Example 1. The resulting purified product was subjected to reversed phase high-performance liquid chromatography for analysis [column: pBondasphere 5μ, C18-100 Å (inner diameter: 3.9 mm, length: 150 mm), manufactured by Waters Corporation; mobile phase: gradient of solvent A containing 0.1% trifluoroacetic acid and solvent B containing 0.1% trifluoroacetic acid and 90% acetonitrile from minute 0 (solvent B=12%) to minute 20 (solvent B=17%); flow rate: 1 ml/min.; detection method: absorbance at wave length of 220 nm]. A single sharp peak appeared at minute 12.8, and the purity was 99%.

Example 3

Assay for Production of Collagen in Skin Fibroblast Using LEH and LEHA (SEQ ID NO: 1)

Fibroblasts derived from human normal skin (CRL-1836; ATCC) were cultured in a 48-well culture plate. More specifically, the cells were plated onto a plate at a density of 12,500 cells/cm2, and cultured at 37° C. for about 72 hours in an atmosphere of 5% carbon dioxide gas and 95% air. As a culture solution, Dulbecco's modified Eagle medium (D-MEM) containing fetal bovine serum (FBS) at a concentration of 10% by weight was used in an amount of 500 μl per well. When the cells reached confluent state, the culture solution was removed, and a medium prepared by adding the LEH or LEHA (SEQ ID NO: 1) synthesized in Example 1 or 2 to D-MEM at a concentration of 10 μg/ml was added thereto in an amount of 500 μl per well. Here, cells to which a medium without adding the peptide was added in an amount of 500 μl per well were used as a control. After 72 hours of culture, the culture solution was collected, and the concentration of type I collagen in the collected culture solution was quantified by enzyme-linked immunosorbent assay (Anti-Human Procollagen type IC-peptide EIA Kit; manufactured by TAKARA BIO INC.). On the basis of the results of the quantification, the amount of type I collagen in the culture solution to which a peptide was added was calculated wherein the amount of type I collagen in the control culture solution is defined as 100%. The results are shown in Table 3.

TABLE 3

| Peptide | Concentration of Peptide (μg/ml) | Amount of Production of Collagen (%) |
|---|---|---|
| Control | 0 | 100 |
| LEH | 10 | 132.2 |
| LEHA | 10 | 137.5 |

As shown in Table 3, it was found that the amount of production of collagen in the fibroblasts derived from human normal skin was significantly increased by culturing the cells in each culture solution to which a peptide was added.

Example 4

Toxicity Test Using LEH and LEHA (SEQ ID NO: 1)

Two-hundred-fifty microliters of D-MEM was added to the cells after the culture solution was collected in Example 3, and subsequently the number of viable cells was counted with Cell Counting Kit-8 (manufactured by DOJINDO LABORATORIES). The results are shown in Table 4.

TABLE 4

| Peptide | Concentration of Peptide (μg/ml) | Number of Viable Cells (cells) |
|---|---|---|
| Control | 0 | $2.8 \times 10^4$ |
| LEH | 10 | $2.8 \times 10^4$ |
| LEHA | 10 | $2.9 \times 10^4$ |

As shown in Table 4, no significant decrease was found in the number of viable cells by culturing the cells in each culture solution to which a peptide was added.

Example 5

Preparation of LEH and LEHA (SEQ ID NO: 1) Peptides from Soy Protein

1) Protease Degradation of Soy Protein

One gram of dehulled soybean powder was dispersed in 40 ml of distilled water, and the pH of the dispersion was adjusted to 8.5 with 0.1 N NaOH. Fifty milligrams of thermolysin (derived from *Bacillus thermoproteolyticus*, trade name: THERMOASE PC10F, manufactured by DAIWA KASEI K.K.) was added thereto, and degradation was carried out at 60° C. for 15 hours. After the reaction, thermolysin was deactivated by boiling the dispersion at 100° C. for 10 minutes. After allowing the dispersion to cool, 1 g of filter aid (trade name: Radiolight 500, manufactured by SHOWA CHEMICAL INDUSTRY CO., LTD) was added thereto, and the mixture was stirred. Thereafter, filtration was carried out.

2) Collection of Crude Peptide

The filtrate obtained as described above was passed through a 150-ml column charged with strong acid ion exchange resin (trade name: "Dowex 50W×2, H+ form, 50-100 mesh", manufactured by The Dow Chemical Company), and the column was washed with deionized water of 5-fold volume of the column, to remove non-peptide components. Components adsorbed to the column were eluted by passing a 2 M ammonia solution through the column, and a peptide fraction was collected. Ammonia was distilled away with an evaporator, and the fraction was further concentrated and dried to solidness. The dried product was dissolved by adding 5 ml of water thereto, and an undissolved substance was removed by carrying out centrifugation (10,000 rpm, 30 minutes). A peptide in the solution was quantified with an analysis kit (trade name: QuantiPro BCA assay kit, SIGMA). As a result, it was confirmed that 140 mg of a crude peptide was collected.

3) Molecular Weight Fractionation

A gel filtration column (φ2.6×100 cm) charged with Sephadex G-25 (Medium type, manufactured by Amersham Biosciences) was equilibrated with 0.1 M sodium phosphate buffer (pH 7.0), and 140 mg of the crude peptide obtained as described above was applied thereto. Elution was carried out at a flow rate of 1.0 ml/min, and with detection at 280 nm, and a fraction having a molecular weight of 1,000 or less was collected. The fraction obtained by collecting was demineralized and concentrated up to a volume of 2 ml.

4) Separation by Strong Acid Ion Exchange Resin

A 20-ml column charged with strong acid ion exchange resin (trade name "SP Sephadex C-25, H+ form", manufactured by Amersham Biosciences) was equilibrated with deionized water, and 2.0 ml of the concentrated fraction having a molecular weight of 1,000 or less obtained as described above was applied thereto. The column was washed with deionized water of 5-fold volume of the column, and a component was eluted with linear gradient of an aqueous solution of sodium chloride of from 0 to 0.256 M. The eluate was collected by a fraction collector in an amount of 2.0 ml for each fraction. In the resulting chromatogram, six major peaks were detected. These six major peaks, specifically, 14 ml of a fraction eluted with sodium chloride at a concentration of from 0.026 to 0.062 M (hereinafter SP [1]), 12 ml of a fraction eluted with sodium chloride at a concentration of from 0.062 to 0.092 M (hereinafter SP [2]), 8 ml of a fraction eluted with sodium chloride at a concentration of from 0.092 to 0.113 M (hereinafter SP [3]), 22 ml of a fraction eluted with sodium chloride at a concentration of from 0.113 to 0.168 M (hereinafter SP [4]), 14 ml of a fraction eluted with sodium chloride at a concentration of from 0.20 to 0.23 M (hereinafter SP [5]), and 16 ml of a fraction eluted with sodium chloride at a concentration of 0.256 M or more (hereinafter SP [6]) were collected, respectively.

5) HPLC Analysis

After demineralization, SP [1] to SP [6] obtained as described above were subjected to HPLC analysis under the following conditions:

(Column) Inertsil ODS-2, φ4.6×250 mm, 5 μm (GL Science Inc.)

(Detection) 214 nm (Flow rate) 1.0 mL/min (Separation Conditions)

Solvent (a): a solution containing 0.05% trifluoroacetic acid

Solvent (b): a solution containing 0.05% trifluoroacetic acid and 20% acetonitrile After equilibration of a column with 100% solvent (a), elution was carried out at a linear gradient so that solvent (b) would be 100% by minute 60.

(Injection volume) 20 μl (Column temperature) Room temperature

Using Leu-Glu-His and Leu-Glu-His-Ala (SEQ ID NO: 1) prepared by chemical synthesis as a standard, elution time of the fraction was compared with that of the standard. As a result, the fraction wherein a peak was detected at the same elution time as the standard was only SP [5], and no significant peak was found at the same elution time as the standard in the fractions other than SP [5].

6) N-Terminal Amino Acid Sequence Analysis

Two peaks in SP [5] detected at the same elution time as the standard were dispensed, and analysis was carried out with N-terminal amino acid sequence analyzer (Procise 494 HT Protein Sequencing Systems, Applied Biosystems). As a result, it was confirmed that these two peaks correspond to Leu-Glu-His and Leu-Glu-His-Ala (SEQ ID NO: 1).

7) Quantification

Calculated from the results of HPLC analysis, it was revealed that when 1 g of dehulled soybean powder was treated with thermolysin, 30.1 µg of Leu-Glu-His and 20.1 µg of Leu-Glu-His-Ala (SEQ ID NO: 1) were generated.

Example 6

Assay for Production of Collagen in Skin Fibroblast Using LEH and LEHA (SEQ ID NO: 1) Derived from Soy Protein Enhancing effect for production of collagen in a skin fibroblast was examined in the same manner as in Example 3, except that the peptide contained in SP [5] fraction obtained in Example 5 was adjusted to have a concentration of 10 µg/ml and used in place of synthesized LEH and LEHA (SEQ ID NO: 1). The results are shown in Table 5.

TABLE 5

| Peptide | Concentration of Peptide (µg/ml) | Amount of Production of Collagen (%) |
|---|---|---|
| Control | 0 | 100 |
| SP [5] | 10 | 177 |

As shown in Table 5, it was found that the amount of production of collagen in the fibroblasts derived from human normal skin was significantly increased by culturing the cells in the culture solution to which SP [5] was added.

Example 7

Toxicity Test Using LEH and LEHA (SEQ ID NO: 1) Derived from Soy Protein

For the cells after the culture solution was collected in Example 6, the number of viable cells was counted in the same manner as in Example 4. The results are shown in Table 6.

TABLE 6

| Peptide | Concentration of Peptide (µg/ml) | Number of Viable Cells (cells) |
|---|---|---|
| Control | 0 | $2.2 \times 10^4$ |
| SP [5] | 10 | $2.2 \times 10^4$ |

As shown in Table 6, no significant decrease was found in the number of viable cells by culturing the cells in the culture solution to which SP [5] was added.

Enhancing effect for production of collagen similar to that exhibited by synthesized LEH and LEHA (SEQ ID NO: 1) peptides is also found in the case where an assay for production of collagen is carried out in the same manner as described above using LEH and LEHA (SEQ ID NO: 1) peptides prepared from soy protein as described in Example 5. In addition, no significant decrease is found in the number of viable cells when a toxicity test is carried out as described above using the LEH and LEHA (SEQ ID NO: 1) peptides prepared from soy protein.

Example 8

Preparation of N-Terminal-Acetylated LEHA (SEQ ID NO: 1)

N-terminal-acetylated derivative of LEHA peptide was prepared following solid-phase synthesis method by Fmoc method (L. A. Carpino, G. Y. Han, J. Am. Chem. Soc., 92, 5748 (1970)). First, the C-terminus of Fmoc-Ala-OH was bound to a resin for solid-phase synthesis, and thereafter the protecting group (Fmoc) was removed by piperidine treatment. Subsequently, this resin was neutralized and washed, and Fmoc-His(1-Trt)-OH was introduced into the N-terminus of Ala. Next, the protecting group (Fmoc) was removed by piperidine treatment, and this resin was neutralized and washed again. Thereafter, Fmoc-Glu(OtBu)-OH was introduced into the N-terminus of His. Next, the protecting group (Fmoc) was removed by piperidine treatment. Subsequently, the resin was neutralized and washed, and N-acetyl-leucine was introduced into the N-terminus of Glu. A peptide chain was cut out from this resin, and deprotection was carried out by cleaving Trt group of His and tBu group of Glu with TFA (trifluoroacetic acid). Finally, purification was carried out by removing an unreacted substance by preparative HPLC, to give LEHA (SEQ ID NO: 1) of which N-terminus was acetylated. The purity of the resulting purified product was 96.8%.

Example 9

Preparation of C-Terminal-Amidated LEHA (SEQ ID NO: 1)

C-terminal-amidated derivative of LEHA peptide was prepared following solid-phase synthesis method by Fmoc method (L. A. Carpino, G. Y. Han, J. Am. Chem. Soc., 92, 5748 (1970)). First, the C-terminus of Fmoc-Ala-OH was bound to 4-methylbenzhydrylamine resin, and thereafter the protecting group (Fmoc) was removed by piperidine treatment. Subsequently, this resin was neutralized and washed, and Fmoc-His(1-Trt)-OH was introduced into the N-terminus of Ala. Next, the protecting group (Fmoc) was removed by piperidine treatment, and this resin was neutralized and washed again. Thereafter, Fmoc-Glu(OtBu)-OH was introduced into the N-terminus of His. Next, the protecting group (Fmoc) was removed by piperidine treatment. Subsequently, the resin was neutralized and washed, and Fmoc-Leu-OH was introduced into the N-terminus of Glu. A peptide chain was cut out from this resin, and deprotection was carried out by cleaving Trt group of His and tBu group of Glu with TFA (trifluoroacetic acid). Finally, purification was carried out by removing an unreacted substance by preparative HPLC, to give LEHA (SEQ ID NO: 1) of which C-terminus was amidated. The purity of the resulting purified product was 94.0%.

Example 10

Assay for Production of Collagen in Skin Fibroblast Using Peptide Derivative

Enhancing effect for production of collagen in a skin fibroblast was examined in the same manner as in Example 3, except that the N-terminal-acetylated LEHA (SEQ ID NO: 1) and C-terminal-amidated LEHA (SEQ ID NO: 1) prepared in Examples 8 and 9 were used in place of the LEH and LEHA (SEQ ID NO: 1) synthesized in Examples 1 and 2. The results are shown in Table 7.

TABLE 7

| Peptide derivative | Concentration of Peptide Derivative (μg/ml) | Amount of Production of Collagen (%) |
|---|---|---|
| Control | 0 | 100 |
| N-terminal-Acetylated-LEHA | 10 | 124 |
| C-terminal-Amidated LEHA | 10 | 121 |

As shown in Table 7, it was found that the amount of production of collagen was significantly increased in the fibroblasts derived from human normal skin by culturing the cells in each culture solution to which a peptide derivative was added.

Example 11

Toxicity Test Using Peptide Derivative

For the cells after the culture solution was collected in Example 10, the number of viable cells was counted as in the same manner in Example 4. The results are shown in Table 8.

TABLE 8

| Peptide derivative | Concentration of Peptide Derivative (μg/ml) | Number of Viable Cells (cells) |
|---|---|---|
| Control | 0 | $2.6 \times 10^4$ |
| N-terminal-Acetylated-LEHA | 10 | $2.8 \times 10^4$ |
| C-terminal-Amidated LEHA | 10 | $2.6 \times 10^4$ |

As shown in Table 8, no significant decrease was found in the number of viable cells by culturing the cells in each culture solution to which a peptide derivative was added.

Example 12

Assay for Production of Hyaluronic Acid in Skin Epidermal Keratinocyte

Normal human epidermal keratinocytes (NHEK, manufactured by KURABO INDUSTRIES LTD.) were cultured in a 48-well culture plate. More specifically, the cells were plated at a density of 25,000 cells/cm2 on a plate, and cultured at 37° C. for about 72 hours in an atmosphere of 5% carbon dioxide gas and 95% air. As a culture solution, HuMedia KG-2 (manufactured by KURABO INDUSTRIES LTD.) was used in an amount of 400 μl per well. The culture solution was removed after 72 hours of culturing, and HuMedia KG-2 medium to which the LEHA (SEQ ID NO: 1) synthesized as described in Example 2 was added at a concentration of 100 or 300 mg/ml was added in an amount of 400 μl per well. Here, cells to which a HuMedia KG-2 without adding LEHA (SEQ ID NO: 1) was added in an amount of 400 μl were used as a control. After additional 72 hours of culturing, the culture solution was collected, and the concentration of hyaluronic acid in the collected culture solution was quantified by enzyme linked immunosorbent assay (hyaluronic acid determination kit; manufactured by Seikagaku Corporation). On the basis of the results of the quantification, the amount of hyaluronic acid in the culture solution to which LEHA (SEQ ID NO: 1) was added was calculated wherein the amount of hyaluronic acid in the control culture solution is defined as 100%. The results are shown in Table 9.

As shown in Table 9, it was found that the amount of production of hyaluronic acid in the normal human epidermal keratinocytes was significantly increased by culturing the cells in the culture solution to which LEHA (SEQ ID NO: 1) was added. Surprisingly, when LEHA (SEQ ID NO: 1) was used at a concentration of 300 μg/ml, remarkably great enhancing effect for production of hyaluronic acid wherein hyaluronic acid is produced in an amount which is about 200% as compared with that in the control was found.

TABLE 9

| Peptide | Concentration of Peptide (μg/ml) | Amount of Production of Hyaluronic Acid (%) |
|---|---|---|
| Control | 0 | 100 |
| LEHA | 100 | 154 |
|  | 300 | 193.3 |

Example 13

Preparation of LEKA (SEQ ID NO: 18)

Peptide LEKA (SEQ ID NO: 18) was prepared in the same manner as in the method described in Example 1. Next, purification was carried out by removing an unreacted substance by preparative HPLC, to give LEKA (SEQ ID NO: 18).

Example 14

Assay for Production of Collagen in Skin Fibroblast Using LEKA (SEQ ID NO: 18)

Enhancing effect for production of collagen in a skin fibroblast was examined in the same manner as in Example 3, except that the LEKA (SEQ ID NO: 18) peptide synthesized as described above was used in place of the LEH and LEHA (SEQ ID NO: 1) synthesized in Examples 1 and 2. The results are shown in Table 10.

TABLE 10

| Peptide | Concentration of Peptide (μg/ml) | Amount of Production of Collagen (%) |
|---|---|---|
| Control | 0 | 100 |
| LEKA | 10 | 112.2 |

As shown in Table 10, it was found that the amount of production of collagen in the fibroblasts derived from normal human skin was increased by culturing the cells in the culture solution to which LEKA (SEQ ID NO: 18) peptide was added.

Example 15

Toxicity Test Using LEKA (SEQ ID NO: 18)

For the cells after the culture solution was collected in Example 14, the number of viable cells was counted in the same manner as in Example 4. The results are shown in Table 11.

TABLE 11

| Peptide | Concentration of Peptide (μg/ml) | Number of Viable Cells (cells) |
|---|---|---|
| Control | 0 | $2.9 \times 10^4$ |
| LEKA | 10 | $3.6 \times 10^4$ |

As shown in Table 11, no decrease was found in the number of viable cells by culturing the cells in the culture solution to which LEKA (SEQ ID NO: 18) was added.

Example 16

Preparation of LDHA (SEQ ID NO: 19)

Peptide LDHA (SEQ ID NO: 19) was synthesized in the same manner as the method described in Example 1. Next, purification was carried out by removing an unreacted substance by preparative HPLC, to give LDHA (SEQ ID NO: 19).

Example 17

Assay for Production of Collagen in Skin Fibroblast Using LDHA (SEQ ID NO: 19)

Enhancing effect for production of collagen in a skin fibroblast was examined in the same manner as in Example 3, except that the LDHA (SEQ ID NO: 19) peptide synthesized as described above was used in an amount of 1 μg/ml in place of the using LEH and LEHA (SEQ ID NO: 1) synthesized in Examples 1 and 2 in an amount of 10 μg/ml. The results are shown in Table 12.

TABLE 12

| Peptide | Concentration of Peptide (μg/ml) | Amount of Production of Collagen (%) |
|---|---|---|
| Control | 0 | 100 |
| LDHA | 1 | 130.5 |

As shown in Table 12, it was found that the amount of production of collagen in the fibroblasts derived from normal human skin was increased by culturing the cells in the culture solution to which LDHA (SEQ ID NO: 19) peptide was added.

Example 18

Toxicity Test Using LDHA (SEQ ID NO: 19)

For the cells after the culture solution was collected in Example 17, the number of viable cells was counted in the same manner as in Example 4. The results are shown in Table 13.

TABLE 13

| Peptide | Concentration of Peptide (μg/ml) | Number of Viable Cells (cells) |
|---|---|---|
| Control | 0 | $3.1 \times 10^4$ |
| LDHA | 1 | $3.3 \times 10^4$ |

As shown in Table 13, no decrease was found in the number of viable cells by culturing the cells in the culture solution to which LDHA (SEQ ID NO: 19) peptide was added.

Example 19

Preparation of LEHAF (SEQ ID NO: 20)

Peptide LEHAF (SEQ ID NO: 20) was synthesized in the same manner as the method described in Example 1. Next, purification was carried out by removing an unreacted substance by preparative HPLC, to give LEHAF (SEQ ID NO: 20).

Example 20

Assay for Production of Collagen in Skin Fibroblast Using LEHAF (SEQ ID NO: 20)

Enhancing effect for production of collagen in a skin fibroblast was examined in the same manner as in Example 3, except that the LEHAF (SEQ ID NO: 20) synthesized as described above was used at a concentration of 1 or 3 μg/ml instead of using the LEH and LEHA (SEQ ID NO: 1) synthesized in Examples 1 and 2 at a concentration of 10 μg/ml. The results are shown in Table 14.

TABLE 14

| Peptide | Concentration of Peptide (μg/ml) | Amount of Production of Collagen (%) |
|---|---|---|
| Control | 0 | 100 |
| LEHAF | 1 | 119.2 |
| LEHAF | 3 | 121.0 |

As shown in Table 14, it was found that the amount of production of collagen in the fibroblasts derived from normal human skin was increased by culturing the cells in the culture solution to which LEHAF (SEQ ID NO: 20) peptide was added.

Example 21

Toxicity Test Using LEHAF (SEQ ID NO: 20)

For the cells after the culture solution was collected in Example 20, the number of viable cells was counted in the same manner as in Example 4. The results are shown in Table 15.

TABLE 15

| Peptide | Concentration of Peptide (μg/ml) | Number of Viable Cells (cells) |
|---|---|---|
| Control | 0 | $3.0 \times 10^4$ |
| LEHAF | 1 | $3.0 \times 10^4$ |
| LEHAF | 3 | $3.0 \times 10^4$ |

As shown in Table 15, no significant decrease was found in the number of viable cells by culturing the cells in the culture solution to which LEHAF (SEQ ID NO: 20) peptide was added.

Example 22

Assay for Anti-Wrinkle Effect Using Hairless Mice

Preventive effect against generation of wrinkle by ultraviolet light using hairless mice is assayed by application test with the peptide. In other words, 5-week old male hairless mice are separated into 3 groups (8 mice/group), and the mice are irradiated with UVB ultraviolet light three times a week over a period of three weeks (at a density of 90 mJ/cm$^2$ in the first week, 120 mJ/cm$^2$ in the second week, and 150 mJ/cm$^2$ in the third week). Fifty microliters of test solution containing each test peptide or the like is applied to back of the hairless mouse in each group three times a day, for the three weeks. After 24 days from the first irradiation with ultraviolet light, wrinkle is visually scored in seven grades (Table 16), to evaluate preventive effect against generation of wrinkle. On the basis of this assay for anti-wrinkle effect, great preventive effect against generation of wrinkle is found in the group to which a test solution containing the peptide of the present invention is applied.

TABLE 16

Score for visual observation of wrinkle, referring to wrinkle-scoring in Photodermatol. Photoimmunol. Photomed 7, 153-158, 1990

| | |
|---|---|
| 0.0 | No remarkable skin groove is found on back skin |
| 0.5 | Remarkable skin groove is partially found on back skin |
| 1.0 | Remarkable skin groove is found throughout back skin |
| 1.5 | Regarding the skin grooves found throughout back skin, transverse skin groove is deeper than longitudinal skin groove |
| 2.0 | Regarding the skin grooves found throughout back skin, transverse skin groove is yet deeper than longitudinal skin groove |
| 2.5 | Wrinkle is found throughout back skin |
| 3.0 | Deep wrinkle is found throughout back skin |

Sequence Listing Free Text

SEQ ID NO: 1 in the Sequence Listing is a peptide of the present invention.

SEQ ID NO: 2 in the Sequence Listing is a DNA encoding LEHA (SEQ ID NO: 1) peptide.

SEQ ID NO: 3 in the Sequence Listing is a DNA encoding LEHA (SEQ ID NO: 1) peptide.

SEQ ID NO: 4 in the Sequence Listing is a DNA encoding LEHA (SEQ ID NO: 1) peptide.

SEQ ID NO: 5 in the Sequence Listing is a DNA encoding LEHA (SEQ ID NO: 1) peptide.

SEQ ID NO: 18 in the Sequence Listing is a peptide of the present invention.

SEQ ID NO: 19 in the Sequence Listing is a peptide of the present invention.

SEQ ID NO: 20 in the Sequence Listing is a peptide of the present invention.

The invention claimed is:

1. A peptide consisting of the sequence:

Leu-Glu-His-Ala (SEQ ID NO: 1)

or its derivative, or a salt thereof, wherein the derivative is obtained by acetylation, palmitoylation, myristylation, amidation, acrylation, dansylation, biotinylation, phosphorylation, succinylation, anilide formation, benzyloxycarbonylation, formylation, nitration, sulfonation, aldehyde formation, cyclization, glycosylation, monomethylation, dimethylation, trimethylation, gaunidylation, amidination, maleylation, trifluoroacetylation, carbamylation, trinitrophenylation, nitrotroponylation, or acetoacetylation of the peptide.

2. A peptide consisting of the sequence:

Leu-Asp-His-Ala (SEQ ID NO: 19)

or its derivative, or a salt thereof, wherein the derivative is obtained by acetylation, palmitoylation, myristylation, amidation, acrylation, dansylation, biotinylation, phosphorylation, succinylation, anilide formation, benzyloxycarbonylation, formylation, nitration, sulfonation, aldehyde formation, cyclization, glycosylation, monomethylation, dimethylation, trimethylation, gaunidylation, amidination, maleylation, trifluoroacetylation, carbamylation, trinitrophenylation, nitrotroponylation, or acetoacetylation of the peptide.

3. A peptide consisting of the sequence:

Leu-Glu-His-Ala-Phe (SEQ ID NO: 20)

or its derivative, or a salt thereof, wherein the derivative is obtained by acetylation, palmitoylation, myristylation, amidation, acrylation, dansylation, biotinylation, phosphorylation, succinylation, anilide formation, benzyloxycarbonylation, formylation, nitration, sulfonation, aldehyde formation, cyclization, glycosylation, monomethylation, dimethylation, trimethylation, gaunidylation, amidination, maleylation, trifluoroacetylation, carbamylation, trinitrophenylation, nitrotroponylation, or acetoacetylation of the peptide.

4. A composition comprising:

the peptide or its derivative, or a salt thereof as in any one of claims 1, 2, and 3; and a pharmaceutically acceptable carrier, a pharmaceutically acceptable base, a cosmetically acceptable carrier, a cosmetically acceptable base, or a food.

5. The composition according to claim 4, wherein the composition is capable of enhancing production of at least one member selected from the group consisting of collagen and hyaluronic acid in a cell.

6. The composition according to claim 4, wherein the composition is suitable for external application to a mammal.

7. The composition according to claim 5, wherein the composition is capable of enhancing production of collagen and/or hyaluronic acid in the cell to at least about 110%.

8. The composition according to claim 4, wherein the peptide derivative or the salt thereof is palmitoylated, N-terminus acetylated, C-terminus amidated or C-terminus methylated.

9. The composition according to claim 4, wherein the composition comprises between 0.0001 and 70% by weight of the peptide or its derivative, or a salt thereof.

10. The composition according to claim 4, comprising at least one of a carrier, a sugar, a cellulose, a poorly water-soluble gum, a cross-linked vinyl polymer, water, a lipid, a base, a fat, an oil, a wax, a fatty acid, a silicone oil, a sterol, an ester, a metallic soap, an alcohol, an additive, a surfactant, a solubilizing component, an emulsifier, an oil component, a stabilizer, a thickener, a preservative, a binder, a lubricant, a dispersing agent, a pH regulator, a moisturizer, an ultraviolet absorbent, a chelating agent, a percutaneous-absorption enhancer, an antioxidant, a disintegrating agent, a plasticizer, a buffer, a vitamin, an amino acid, a coloring agent, a perfuming agent, a skin-lightening component, an anti-inflammatory component, an antibiotic component, a cell-activating component, an astringent component, an antioxidant component, an acne-ameliorating component, a component for enhancing synthesis of a biological component, a component for enhancing circulation, a moisturizing component, and an anti-aging component.

11. The composition according to claim 4, wherein the composition is in the form of a liquid, an emulsion, a cream, a lotion, a paste, a mousse, a gel, a sheet, an aerosol, a spray, a food, a feed, a tablet, a pill, granules, fine granules, a powder, a hard capsule, a soft capsule, a dry syrup, a solution, a gel preparation, a liposome preparation, an extract preparation, a tincture, a lemonade preparation, or a jelly preparation.

12. The composition according to claim 4, wherein the composition is capable of preventing and/or ameliorating wrinkles or sagging of skin, ameliorating a decrease in elasticity or decrease in tautness of skin, ameliorating an articular disease, or ameliorating a corneal disorder, when administered to a subject.

* * * * *

```
SEQUENCE LISTING

<160> NUMBER OF SEQ ID NOS: 62

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide of the present invention

<400> SEQUENCE: 1

Leu Glu His Ala
1

<210> SEQ ID NO 2
<211> LENGTH: 12
<212> TYPE: DNA
<213> ORGANISM: Artificial Sequence
<220> FEATURE:
<223> OTHER INFORMATION: Synthetic DNA encoding LEHA peptide

<400> SEQUENCE: 2
ttggaacatg cg                                                         12

<210> SEQ ID NO 3
<211> LENGTH: 12
<212> TYPE: DNA
<213> ORGANISM: Artificial Sequence
<220> FEATURE:
<223> OTHER INFORMATION: Synthetic DNA encoding LEHA peptide
```

```
<400> SEQUENCE: 3
ttggaacatg ca                                                         12

<210> SEQ ID NO 4
<211> LENGTH: 12
<212> TYPE: DNA
<213> ORGANISM: Artificial Sequence
<220> FEATURE:
<223> OTHER INFORMATION: Synthetic DNA encoding LEHA peptide

<400> SEQUENCE: 4
cttgaacacg cg                                                         12

<210> SEQ ID NO 5
<211> LENGTH: 12
<212> TYPE: DNA
<213> ORGANISM: Artificial Sequence
<220> FEATURE:
<223> OTHER INFORMATION: Synthetic DNA encoding LEHA peptide

<400> SEQUENCE: 5
ctggagcacg ca                                                         12

<210> SEQ ID NO 6
<211> LENGTH: 14
<212> TYPE: PRT
<213> ORGANISM: Daucus carota

<400> SEQUENCE: 6

Leu Pro Ser Arg Asp Leu Glu His Ala Ser Ser Tyr Thr Pro
1               5                   10

<210> SEQ ID NO 7
<211> LENGTH: 14
<212> TYPE: PRT
<213> ORGANISM: Lycopersicon esculentum

<400> SEQUENCE: 7

Ile Phe Gly Ser Pro Leu Glu His Ala Arg Gln Leu Trp Pro
1               5                   10

<210> SEQ ID NO 8
<211> LENGTH: 14
<212> TYPE: PRT
<213> ORGANISM: Solanum tuberosum

<400> SEQUENCE: 8

Val Val Arg Cys Cys Leu Glu His Ala Ala Ser Val Ala Lys
1               5                   10

<210> SEQ ID NO 9
<211> LENGTH: 14
<212> TYPE: PRT
<213> ORGANISM: Oryza sativa

<400> SEQUENCE: 9

Val Val Arg Cys Cys Leu Glu His Ala Ala Ser Val Ala Lys
1               5                   10

<210> SEQ ID NO 10
<211> LENGTH: 14
<212> TYPE: PRT
<213> ORGANISM: Glycine max

<400> SEQUENCE: 10
```

```
Phe Ala Pro Glu Phe Leu Glu His Ala Phe Val Val Asp Arg
1               5                   10
```

<210> SEQ ID NO 11
<211> LENGTH: 14
<212> TYPE: PRT
<213> ORGANISM: Phaseolus vulgaris

<400> SEQUENCE: 11

```
Glu Val Glu Val Gln Leu Glu His Ala Leu Ser Met Gln Glu
1               5                   10
```

<210> SEQ ID NO 12
<211> LENGTH: 14
<212> TYPE: PRT
<213> ORGANISM: Manihot esculenta

<400> SEQUENCE: 12

```
Pro Gln Val Glu Ile Leu Glu His Ala Ala Leu Gly Val Phe
1               5                   10
```

<210> SEQ ID NO 13
<211> LENGTH: 14
<212> TYPE: PRT
<213> ORGANISM: Prunus persica

<400> SEQUENCE: 13

```
Thr Gly Ser Trp Thr Leu Glu His Ala Lys Leu Lys Ala Arg
1               5                   10
```

<210> SEQ ID NO 14
<211> LENGTH: 14
<212> TYPE: PRT
<213> ORGANISM: Fragaria x ananassa

<400> SEQUENCE: 14

```
Glu Ile Ala Asn Ala Leu Glu His Ala Gly His Arg Phe Leu
1               5                   10
```

<210> SEQ ID NO 15
<211> LENGTH: 14
<212> TYPE: PRT
<213> ORGANISM: Strongylocentrotus purpuratus

<400> SEQUENCE: 15

```
Val Ala Ile Asn Gly Leu Glu His Ala His Trp Trp Glu Gln
1               5                   10
```

<210> SEQ ID NO 16
<211> LENGTH: 14
<212> TYPE: PRT
<213> ORGANISM: Lethenteron japonicum

<400> SEQUENCE: 16

```
Ser Gln Leu Leu Arg Leu Glu His Ala Phe Glu Lys Asn His
1               5                   10
```

<210> SEQ ID NO 17
<211> LENGTH: 14
<212> TYPE: PRT
<213> ORGANISM: Mytilus galloprovincialis

<400> SEQUENCE: 17

```
Asp Ala Arg Ser Leu Leu Glu His Ala Glu Arg Ala Arg Lys
1               5                   10
```

```
<210> SEQ ID NO 18
<211> LENGTH: 4
<212> TYPE: PRT
<213> ORGANISM: Artificial Sequence
<220> FEATURE:
<223> OTHER INFORMATION: Synthetic peptide of the present invention

<400> SEQUENCE: 18

Leu Glu Lys Ala
 1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide of the present invention

<400> SEQUENCE: 19

Leu Asp His Ala
 1

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide of the present invention

<400> SEQUENCE: 20

Leu Glu His Ala Phe
 1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Lys Thr Thr Lys Ser
 1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Leu Glu His Trp
 1

<210> SEQ ID NO 23
<211> LENGTH: 4
<212> TYPE: PRT
<213> ORGANISM: Artificial Sequence
<220> FEATURE:
<223> OTHER INFORMATION: Synthetic peptide

<400> SEQUENCE: 23

Leu Glu His Phe
 1
```

```
<210> SEQ ID NO 24
<211> LENGTH: 4
<212> TYPE: PRT
<213> ORGANISM: Artificial Sequence
<220> FEATURE:
<223> OTHER INFORMATION: Synthetic peptide

<400> SEQUENCE: 24

Leu Glu His Val
1

<210> SEQ ID NO 25
<211> LENGTH: 4
<212> TYPE: PRT
<213> ORGANISM: Artificial Sequence
<220> FEATURE:
<223> OTHER INFORMATION: Synthetic peptide

<400> SEQUENCE: 25

Leu Glu His Leu
1

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide

<400> SEQUENCE: 26

Leu Glu His Ile
1

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide

<400> SEQUENCE: 27

Leu Glu His Met
1

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Leu Glu His Gly
1

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide

<400> SEQUENCE: 29

Leu Glu His Ser
1

<210> SEQ ID NO 30
<211> LENGTH: 4
```

```
<212> TYPE: PRT
<213> ORGANISM: Artificial Sequence
<220> FEATURE:
<223> OTHER INFORMATION: Synthetic peptide

<400> SEQUENCE: 30

Leu Glu His Thr
1

<210> SEQ ID NO 31
<211> LENGTH: 4
<212> TYPE: PRT
<213> ORGANISM: Artificial Sequence
<220> FEATURE:
<223> OTHER INFORMATION: Synthetic peptide

<400> SEQUENCE: 31

Ala Leu Glu His
1

<210> SEQ ID NO 32
<211> LENGTH: 4
<212> TYPE: PRT
<213> ORGANISM: Artificial Sequence
<220> FEATURE:
<223> OTHER INFORMATION: Synthetic peptide

<400> SEQUENCE: 32

Gly Leu Glu His
1

<210> SEQ ID NO 33
<211> LENGTH: 4
<212> TYPE: PRT
<213> ORGANISM: Artificial Sequence
<220> FEATURE:
<223> OTHER INFORMATION: Synthetic peptide

<400> SEQUENCE: 33

Ser Leu Glu His
1

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Met Leu Glu His
1

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Thr Leu Glu His
1

<210> SEQ ID NO 36
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 36

Leu Glu His Ala Trp
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Leu Glu His Ala Val
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Leu Glu His Ala Leu
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Leu Glu His Ala Ile
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Leu Glu His Ala Met
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Leu Glu His Ala Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 42

Leu Glu His Ala Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide

<400> SEQUENCE: 43

Leu Glu His Ala Thr
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Ala Leu Glu His Ala
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Gly Leu Glu His Ala
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Ser Leu Glu His Ala
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide

<400> SEQUENCE: 47

Met Leu Glu His Ala
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide

<400> SEQUENCE: 48
```

Thr Leu Glu His Ala
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

Phe Leu Glu His Ala
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide

<400> SEQUENCE: 50

Ser Leu Glu His His Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Gly Leu Glu His Ala Leu
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide

<400> SEQUENCE: 52

Asp Leu Glu His Ala Leu
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide

<400> SEQUENCE: 53

Gln Leu Glu His Ala Lys
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide

<400> SEQUENCE: 54

Ser Leu Glu His Ala Asp

<210> SEQ ID NO 55
<211> LENGTH: 6
<212> TYPE: PRT
<213> ORGANISM: Artificial Sequence
<220> FEATURE:
<223> OTHER INFORMATION: Synthetic peptide

<400> SEQUENCE: 55

Gln Leu Glu His Ala Arg
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide

<400> SEQUENCE: 56

Glu Phe Leu Glu His Ala
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide

<400> SEQUENCE: 57

Leu Glu His Ala Val Val
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Asp Pro Glu Leu Glu His Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

His Leu Glu His Ala Ala Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Leu Glu His Ala Ser Val Asp
1               5

```
<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61

Ile Glu His Ala
1

<210> SEQ ID NO 62
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Leu Asp Lys Ala
1
```